US00RE50189E

(19) United States
(12) Reissued Patent
Baert et al.

(10) Patent Number: US RE50,189 E
(45) Date of Reissued Patent: Oct. 29, 2024

(54) LONG TERM TREATMENT OF HIV-INFECTION WITH TMC278

(71) Applicant: Janssen Sciences Ireland Unlimited Company, County Cork (IE)

(72) Inventors: Lieven Elvire Colette Baert, Bruges (BE); Guenter Kraus, Sint-Katelijne-Waver (BE); Gerben Albert Eleutherius Van 'T Klooster, Breda (NL)

(73) Assignee: Janssen Sciences Ireland Unlimited Company, County Cork (IE)

(21) Appl. No.: 17/473,424

(22) Filed: Sep. 13, 2021

Related U.S. Patent Documents

Reissue of:
(64) Patent No.: 10,953,009
Issued: Mar. 23, 2021
Appl. No.: 12/161,445
PCT Filed: Jan. 19, 2007
PCT No.: PCT/EP2007/050516
§ 371 (c)(1),
(2) Date: Apr. 12, 2011
PCT Pub. No.: WO2007/082922
PCT Pub. Date: Jul. 26, 2007

(30) Foreign Application Priority Data

Jan. 20, 2006 (EP) ..... 06100677

(51) Int. Cl.
*A61K 31/505* (2006.01)
*A61P 31/00* (2006.01)
*A61P 31/18* (2006.01)

(52) U.S. Cl.
CPC ..... *A61K 31/505* (2013.01); *A61P 31/00* (2018.01); *A61P 31/18* (2018.01)

(58) Field of Classification Search
CPC ..... A61K 31/505; A61P 31/00
See application file for complete search history.

(56) References Cited

U.S. PATENT DOCUMENTS

| | | | |
|---|---|---|---|
| 6,221,400 B1 | 4/2001 | Liversidge et al. | |
| 6,555,544 B2 | 4/2003 | Fran et al. | |
| 8,426,434 B2 | 4/2013 | Stokbroekx et al. | |
| 10,765,674 B2 | 9/2020 | Baert et al. | |
| 10,953,009 B2 | 3/2021 | Baert et al. | |
| 11,389,447 B2 | 7/2022 | Baert et al. | |
| 2004/0115268 A1 | 6/2004 | Ashton et al. | |
| 2004/0127422 A1* | 7/2004 | Buelow | A61K 38/08 514/3.85 |
| 2004/0198739 A1 | 10/2004 | Guillemont et al. | |
| 2006/0111379 A1 | 5/2006 | Guillemont et al. | |

FOREIGN PATENT DOCUMENTS

| | | |
|---|---|---|
| EP | 0499299 A | 8/1992 |
| EP | 1214059 B | 6/2002 |
| EP | 1 632 232 A1 | 3/2006 |
| JP | 06316524 | 11/1994 |
| WO | WO 2001/010456 | 2/2001 |
| WO | WO 2001/074329 | 10/2001 |
| WO | 2003/016306 A1 | 2/2003 |
| WO | WO 03/016306 A1 | 2/2003 |
| WO | WO 2003/043586 A | 5/2003 |
| WO | WO 2004/043433 | 5/2004 |
| WO | WO 2004/046309 | 6/2004 |
| WO | WO 2004/069812 | 8/2004 |
| WO | WO 2004/073703 | 9/2004 |
| WO | 2005/021001 A1 | 3/2005 |
| WO | WO 05/021001 A1 | 3/2005 |
| WO | WO 2006/055603 A | 5/2006 |
| WO | 2006/106103 A2 | 10/2006 |
| WO | WO 06/106103 A2 | 10/2006 |
| WO | WO 2007/082922 A2 | 7/2007 |
| WO | WO 2007/147882 | 12/2007 |

OTHER PUBLICATIONS

Acknowledgement of Receipt issued by the EPO for EP06115938, date of receipt Jun. 23, 2006.
Aulton, Michael E., Pharmaceutics, The Science of Dosage Form Design, 2nd Edition, Table of Contents (2002).
Baert, Lieven et al., Development of a long-acting injectable formulation with nanoparticles of rilpivirine (TMC278) for HIV treatment, European Journal of Pharmaceutics and Biopharmaceutics 72 (2009) pp. 502-508.
Caelyx package leaflet, May 23, 2006.
Declaration: Entitlement to apply for and be granted a patent in relation to International Application No. PCT/EP2007/056230, filed Jul. 24, 2007, published Dec. 27, 2007.
Edurant package leaflet, Nov. 30, 2011.
Eldred et al., Journal of Acquired Immune Deficiency Syndromes and Human Retroviroloqy, vol. 18, No. 2, Jun. 1, 1998, pp. 117-125.
Extract from Organic Chemistry by Clayden, Greeves, Warren and Wothers, pp. 583-585; 748-749; 758-759 (2004).
Farquhar, Cary, et al., "Salivary Secretary of Leukocyte Protease Inhibitor is Associated With Reduced Transmission of Human Immunodeficiency Virus Type 1 Through Breast Milk", The Journal of Infectious Diseases, 2002, vol. 186, pp. 1173-1176, Infectious Diseases Society of America.
Frampton & Croom, "Efavirenz/Emtricitabine/Tenofovir Disoproxil Fumarate" Drugs 66, 1501-1512 (2006).
Gallant et al., J. Int. Assoc. Physicians AIDS Care, May 1998, 4(5): 32-5 (abstract only).
Golin et al., J. Gen. Intern. Med., Oct. 2002, vol. 17, pp. 756-765.
Gregoriadis, et al., "Targeting of Drugs 6 Strategies for Stealth Therapeutic Systems," Life Science, 300: 4-5 (1998).
Gregoriadis, G. et al. (eds.), "Coating of Nanoparticles With Surfactants: Targeting Versus Prolonged Circulation", *Targeting of Drugs 6*, (1998), pp. 253-261.

(Continued)

*Primary Examiner* — Padmashri Ponnaluri
(74) *Attorney, Agent, or Firm* — Sofia Kopelevich

(57) ABSTRACT

This invention relates to the use of a parenteral formulation comprising an anti-virally effective amount of TMC278 or a pharmaceutically acceptable acid-addition salt thereof, and a carrier, for the manufacture of a medicament for the treatment of a subject being infected with HIV, wherein the formulation is to be administered intermittently at a time interval of at least one week.

64 Claims, No Drawings

(56) References Cited

OTHER PUBLICATIONS

Gulick R.M. : 'New Antiretroviral Drugs', Clinical Microbiology and Infection, vol. 9, 2003, pp. 186-193.
Haldol® decanoate FDA approval material, Center for Drug Evaluation and Research, Approval Package, Jan. 30, 1998.
Jackson et al., "Rilpavirine-LA Formulation: Pharmacokinetics in Plasma, Genital Tract in HIV Females and Rectum in Males", Paper #35, CROI 2012 Seattle, Washington State Convention Center, Mar. 5-8, 2012, 2pgs.
Janssen Press Release dated Aug. 15, 2018, Janssen Reports Positive Topline Results for Atlas Phase III Study of a Novel, Long Acting injectable Two-Drug Regimen for the Treatment of HIV-1.
Janssen Press Release dated Apr. 29, 2019, Janssen Announces Submission of New Drug Application to U.S. FDA For the First Monthly, Injectable, Two-Drug Regimen of Rilpivirine and Cabotegravir for Treatment of HIV.
JATO: Pharmaceutical Technology, vol. II, Chapter 3: Injectables, pp. 157-249 (Nov. 30, 1999).
McNeely, Tessie B., et al., "Secretory Leukocyte Protease Inhibitor: A Human Saliva Protein Exhibiting Anti-Human Immunodeficiency Virus 1 Activity In Vitro", The Journal of Clinical Investigation, Inc., 1995, vol. 96, pp. 456-464.
Merisko-Liversidge et al., "Nanosizing: a formulation approach for poorly-water-soluble compounds", European Journal of Pharmaceutical Sciences, vol. 18, pp. 113-120 (2003) (XP002399359).
Müller et al., "Nanosuspensions as particulate drug formulations in therapy Rationale for development and what we can expect for the future", Advanced Drug Delivery Reviews, vol. 47, No. 1, pp. 3-19 (2001) (XP002232883).
NIH Guidelines for the Use of Antiretroviral Agents in H IV-1-Infected Adults and Adolescent dated May 4, 2006.
Notice of Opposition in European Patent No. EP2040671 dated Oct. 30, 2018 (16 pages).
Okwundu et al., "Antiretroviral pre-exposure prophylaxis (PrEP) for preventing HIV in high-risk individuals", the Cochrane Library, Issue 4, p. 1-23, 2009.
Opposition Decision, EP1827500, T 2506/12, Oct. 4, 2016.
Patent Assignment from Janssen Pharmaceutica NV to Tibotec Pharmaceuticals Limited executed Jul. 23, 2007 for U.S. Appl. No. 12/305,276.
Patent Assignment from Tibotec BVBA to Tibotec Pharmaceuticals Limited executed Jul. 23, 2007 for U.S. Appl. No. 12/305,276.
PCT Request Form for International Application No. PCT/EP2007/056230, International Filing Date Jun. 22, 2007.
Priority document downloaded from EPO Register in Patent Application No. 06115938.0/EP06115938 with a filing date on EPO Register of Jun. 22, 2007 (priority document EP06115938 having a filing date of Jun. 23, 2006, and a publication date of Dec. 27, 2007).
Rabinow, Barrett E., "Nanosuspensions in Drug Delivery", Nature Reviews, Sep. 2004, vol. 3, pp. 785-796.
Remington, *Farmacia*, 20$^{th}$ Edition, Chapter 22 (2003).
Remington, The Science and Practice of Pharmacy, 21$^{st}$ Edition, pp. 314, 320, 749, 766, 955, 1072 (2005).
Request for grant of a European patent for EP06115938 printed on Jun. 23, 2006.
Risperdal Consta® product information, Janssen, L.P., Mar. 2006.
Romano et al., "Pharmacokinetics and Pharmacodynamics in HIV Prevention; Current Status and Further Directions: A Summary of the DAIDS and BMGF Sponsored Think Tank on Pharmacokinetics (PK)/Pharmacodynamics (PD) in HIV Prevention", AIDS Research and Human Retroviruses, 29(11), p. 1418-1427, 2013.
Silvestri, et al., "Current state-of-the-art in preclinical and clinical development of novel nonnucleotide HIV-1 reverse transcriptase inhibitors," Expert Opinion on Therapeutic Patents, 16(7): 939-962 (2006).
Tan et al., "Surface modification of nanoparticles by PEO/PPO block copolymers to minimize interactions with blood components and prolong blood circulation in rats", *Biomaterials* 1993, vol. 14, No. 11, pp. 823-833.
The PRN Notebook®; vol. 11, No. 2; Oct. 2006, pp. 2-7.
Torchilin, V., Nature Reviews, "Recent Advances with Liposomes as Pharmaceutical Carriers", vol. 4, pp. 145-160, Feb. 2005.
Uranyl Acetate MSDS (2006), EMS Catalog No. 22400, Dated May 15, 2006.
Van Eerdenbrugh et al., "Characterization of physico-chemical properties and pharmaceutical performance of sucrose co-freeze-dried solid nanoparticulate powders of the anti-HIV agent loviride prepared by media milling", International Journal of Pharmaceutics, vol. 338, No. 1-2, pp. 198-206 (2007) (XP022093455).
Verloes, R. et al., "Safety, Tolerability and Pharmacokinetics of Rilpivirine Following Administration of a Long-Acting Formulation in Healthy Volunteers", *HIV Medicine* (2015), 16, pp. 477-484.
Wahl, Sharon M., "Anatomic Dissociation between HIV-1 and Its Endogenous Inhibitor in Mucosal Tissues", American Journal of Pathology, 1997, vol. 150, No. 4, pp. 1275-1284, American Society for Investigative Pathology.
International search report dated Jul. 3, 2007 for corresponding international application PCT/EP2007/050516.
International search report dated Apr. 28, 2008, for corresponding international application PCT/EP2007/056230.
International Search Report dated Mar. 27, 2007, for Corresponding International Application PCT/EP2006/061303.
Written Opinion dated Mar. 27, 2007, for Corresponding International Application PCT/EP2006/061303.
Susman, E. "Retroviruses and Opportunistic Infections", Idrugs, Current Drugs Ltd., vol. 8, No. 4, pp. 299-302 (2005).
Janssen et al., In Search of a Novel Anti-HIV Drug: Multidisciplinary Coordination in the Discovery of 4-[[4-[[4-(1E)-2-Cyanoethenyl]-2,6-dimethylphenyl]amino]-2-pyrimidinyl]amino]benzonitrile (R278474, Rilpivirine), J. Med. Chem., vol. 48, pp. 1901-1909 (2005).
Goebel et al., "Short-term antiviral activity of TMC278—a novel NNRTI—in treatment-naive HIV-1-infected subjects", AIDS, 2006, vol. 20, No. 13, 1721-1726.
Gongfu et al., "Manual for prevention and Treatment of Toxic Side Effect of Drugs", Peking Union Medical College Press, Dec. 31, 2004, 5 pages.
Shilong, "Study of Clinical Science Research Method for Chinese and Western Medicine", Science Press, Aug. 31, 2003, 5 pages.

* cited by examiner

LONG TERM TREATMENT OF HIV-INFECTION WITH TMC278

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application is a national stage application of Patent Application No. PCT/EP2007/050516, filed Jan. 19, 2007, which application claims priority from EPO Patent Application No. 06100677.1, filed Jan. 20, 2006, both of which are hereby incorporated by reference in their entirety.

FIELD OF THE INVENTION

This invention relates to the long term treatment of HIV infection by intermittently administering a parenteral formulation comprising the NNRTI TMC278 at relatively long time intervals.

BACKGROUND OF THE INVENTION

The treatment of Human Immunodeficiency Virus (HIV) infection, known as cause of the acquired immunodeficiency syndrome (AIDS), remains a major medical challenge. HIV is able to evade immunological pressure, to adapt to a variety of cell types and growth conditions and to develop resistance against currently available drug therapies. The latter include nucleoside reverse transcriptase inhibitors (NRTIs), non-nucleoside reverse transcriptase inhibitors (NNRTIs), nucleotide reverse transcriptase inhibitors (NtRTIs), HIV-protease inhibitors (PIs) and the more recent fusion inhibitors.

Although effective in suppressing HIV, each of these drugs, when used alone, is confronted with the emergence of resistant mutants. This led to the introduction of combination therapy of several anti-HIV agents usually having a different activity profile. In particular the introduction of "HAART" (Highly Active Anti-Retroviral Therapy) resulted in a remarkable improvement in anti-HIV therapy, leading to a large reduction in HIV-associated morbity and mortality. Current guidelines for antiretroviral therapy recommend such triple combination therapy regimen even for initial treatment. However, none of the currently available drug therapies is capable of completely eradicating HIV. Even HAART can face the emergence of resistance, often due to non-adherence and non-persistence with antiretroviral therapy. In these cases HAART can be made effective again by replacing one of its components by one of another class. If applied correctly, treatment with HAART combinations can suppress the virus for many years, up to decades, to a level where it no longer can cause the outbreak of AIDS.

One class of HIV drugs often used in HAART is that of the NNRTIs, a number of which are currently on the market and several others are in various stages of development. An NNRTI currently in development is the compound 4-[[4-[[4-(2-cyanoethenyl)-2,6-dimethylphenyl]-amino]-2-pyrimidinyl]-amino]-benzonitrile, also referred to as TMC278. This compound not only shows pronounced activity against wild type HIV, but also against many of its mutated variants.

The compound TMC278, its pharmacological activity as well as a number of procedures for its preparation have been described in WO-03/16306. Various conventional pharmaceutical dosage forms, including tablets, capsules, drops, suppositories, oral solutions and injectable solutions are exemplified therein.

Because of their pharmacokinetic properties and the need to keep plasma levels above a minimum level, currently used anti-HIV drugs require frequent administration of relatively high doses. The number and/or volume of dosage forms that need to be administered are commonly referred to as the "pill burden". A high pill burden is undesirable for many reasons, such as the frequency of intake, often combined with the inconvenience of having to swallow large dosage forms, as well as the need to store and transport a large number or volume of pills. A high pill burden increases the risk of patients not taking their entire dose, thereby failing to comply with the prescribed dosage regimen. As well as reducing the effectiveness of the treatment, this also leads to the emergence of viral resistance. The problems associated with a high pill burden are multiplied where a patient must take a combination of different anti-HIV agents.

Therefore, it would be desirable to provide HIV inhibitory therapy that reduces pill burden in that it involves the administration of dosage forms of relatively small size and additionally does not require frequent dosing. It would be attractive to provide anti-HIV therapy involving the administration of dosage forms at long time intervals such as one week or longer, or even one month or longer.

It now has been found that the intermittent administration of parenteral formulations of the NNRTI TMC278 at time intervals of one week or longer such as up to one year, results in plasma levels that are adequate in suppressing HIV. This allows for a reduced number of administrations thereby being beneficial in terms of pill burden and drug compliance of the patient.

SUMMARY OF THE INVENTION

In one aspect the present invention relates to the use of a parenteral formulation comprising an anti-virally effective amount of TMC278 or a pharmaceutically acceptable acid-addition salt thereof, and a carrier, for the manufacture of a medicament for the treatment of a subject infected with HIV, wherein the formulation is to be administered intermittently at a time interval that is in the range of one week to one year. Or, the present invention relates to the use of a parenteral formulation comprising an anti-virally effective amount of TMC278 or a pharmaceutically acceptable acid-addition salt thereof, and a carrier, for the treatment of a subject infected with HIV, wherein the formulation is to be administered intermittently at a time interval that is in the range of one week to one year.

In another aspect, there is provided a method of treating a subject infected with HIV, said method comprising the administration of a parenteral formulation comprising an anti-virally effective amount of TMC278 or a pharmaceutically acceptable acid-addition salt thereof, and a carrier, wherein the formulation is administered intermittently at a time interval that is in the range of one week to one year.

In one embodiment the invention concerns a use or a method as specified herein, wherein the parenteral formulation is administered or is to be administered at a time interval that is in the range of one week to one month, or in the range of one month to three months, or in the range of three months to six months, or in the range of six months to twelf months.

In another embodiment the invention concerns a use or a method as specified herein, wherein the parenteral formulation is administered or is to be administered once every two weeks, or once every month, or once every three months.

DETAILED DESCRIPTION OF THE INVENTION

The compound used in the invention is 4-[[4-[[4-(2-cyanoethenyl)-2,6-dimethylphenyl]amino]-2-pyrimidinyl]amino]benzonitrile, having the generic name rilpivirine, also known as TMC278 (or previously referred to as R278474). TMC278 is in clinical development as a HIV inhibitor belonging to the class of the NNRTIs.

TMC278 can be used in base form or as a pharmaceutically acceptable salt form, in particular as an acid addition salt form. The pharmaceutically acceptable addition salts are meant to comprise the therapeutically active non-toxic salt forms. The acid addition salt forms can be obtained by treating the base form with appropriate acids as inorganic acids, for example, hydrohalic acids, e.g. hydrochloric, hydrobromic, and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic, and the like acids.

The term addition salts also comprises the hydrates and the solvent addition forms that can be derived of the compound TMC278. Examples of such forms are e.g. hydrates, alcoholates, and the like.

TMC278 occurs in stereoisomeric forms, more in particular as E- and Z-isomeric forms. Both isomers may be used in the present invention. Whenever reference is made herein to TMC278, the E- or the Z-form as well as any mixture of both forms are meant to be included. A preferred form of TMC278 for use in the invention is the E-isomer, i.e. (E)-4-[[4-[[4-(2-cyanoethenyl)-2,6-dimethylphenyl]-amino]-2-pyrimidinyl]-amino]-benzonitrile, which may be referred to as E-TMC278. The Z-isomer of TMC278, i.e. (Z)-4-[[4-[[4-(2-cyanoethenyl)-2,6-dimethylphenyl]-amino]-2-pyrimidinyl]-amino]-benzonitrile, which may be referred to as Z-TMC278), can also be used.

Whenever reference is made herein to the E-form of TMC278 (i.e. E-TMC278), the pure E-isomer or any isomeric mixture of the E- and the Z-forms wherein the E-form is predominantly present is meant to be comprised, i.e. an isomeric mixture containing more than 50% or in particular more than 80% of the E-form, or even more than 90% of the E-form. Of particular interest is the E-form substantially free of the Z-form. Substantially free in this context refers to E-Z-mixtures with no or almost no Z-form, e.g. isomeric mixtures containing as much as 90%, in particular 95% or even 98% or 99% of the E-form. Equally, whenever reference is made herein to the Z-form of TMC278 (i.e. Z-TMC278), the pure Z-isomer or any isomeric mixture of the Z- and the E-forms wherein the Z-form is predominantly present is meant to be comprised, i.e. an isomeric mixture containing more than 50% or in particular more than 80% of the Z-form, or even more than 90% of the Z-form. Of particular interest is the Z-form substantially free of the E-form. Substantially free in this context refers to E-Z-mixtures with no or almost no E-form, e.g. isomeric mixtures containing as much as 90%, in particular 95% or even 98% or 99% of the Z-form.

Also meant to be included for use in this invention are salts of the stereoisomeric forms of TMC278, in particular the salts mentioned above of Z-TMC278 or of E-TMC278.

Whenever used herein, the term "TMC278" refers to as well the base form as any pharmaceutically acceptable acid-addition salt thereof, and also to the stereoisomeric forms of TMC278 as well as any pharmaceutically acceptable acid-addition salt of said stereoisomeric forms. In particular, the term "TMC278" refers to the E-isomer of TMC278 as well as its pharmaceutically acceptable acid-addition salts.

The administration of TMC278 as in the present invention may suffice to treat HIV infection, but in a number of cases it may be recommendable to co-administer other HIV inhibitors. The latter preferably include HIV inhibitors of other classes, in particular those selected from NRTIs, PIs and fusion inhibitors. In one embodiment, the other HIV inhibitor that is co-administered is a PI. In another embodiment, the other HIV inhibitor that is co-administered is a NRTI. HIV inhibitors that may be co-administered may be those used in HAART combinations comprising an NNRTI. For example two further NRTIs or an NRTI and a PI may be co-administered. Such co-administration may be by oral administration or parenterally.

In certain instances, the treatment of HIV infection may be limited to only the administration of a parenteral formulation of TMC278 in accordance with the methodology of this invention, i.e. as monotherapy without co-administration of further HIV inhibitors. This option may be recommended, for example, where the viral load is relatively low, for example where the viral load (represented as the number of copies of viral RNA in a specified volume of serum) is below about 200 copies/ml, in particular below about 100 copies/ml, more in particular below 50 copies/ml, specifically below the detection limit of the virus. In one embodiment, this type of monotherapy is applied after initial treatment with a combination of HIV drugs, in particular with any of the HAART combinations during a certain period of time until the viral load in blood plasma reaches the afore mentioned low viral level.

Thus, in a further aspect the present invention relates to the use of a parenteral formulation comprising an antivirally effective amount of TMC278 or a pharmaceutically acceptable acid-addition salt thereof, and a carrier, for treating a subject infected with HIV, or for the manufacture of a medicament for treating a subject infected with HIV, wherein the formulation is to be administered after treatment of said subject with a combination of HIV inhibitors and the formulation is administered intermittently at a time interval that is in the range of one week to one year.

Or in a further aspect, the present invention provides a method for the long term treatment of a subject infected with HIV, said method comprising (i) the treatment of said subject with a combination of HIV inhibitors; followed by (ii) the intermittent administration of a parenteral formulation comprising an effective amount of TMC278 or a pharmaceutically acceptable acid-addition salt thereof, and a carrier, wherein the formulation is administered at a time interval that is in the range of one week to one year.

In one embodiment, in the use or method mentioned in the previous two paragraphs, the intermittent treatment with a parenteral formulation of TMC278 is or is to be started after the treatment with a combination of anti-HIV drugs reducing the viral load to below about 200 copies/ml, in particular below about 100 copies/ml, more in particular below 50 copies/ml, or below the detection limit of the virus.

The parenteral formulations of TMC278 are administered intermittently at a time interval of at least one week, or in particular at a time interval mentioned herein, meaning that the parenteral formulation is administered without any interjacent additional administrations of TMC278. Or with other words, TMC278 is administered at particular points in time separated from one another by a time period of at least one week, or in particular at a time interval mentioned herein, during which no TMC278 is administered. Hence the administration schedule is simple, requiring few administrations, and therefore dramatically reduces the problem of "pill burden" faced with standard HIV medication. This in turn will improve the patient's compliance to the prescribed medication.

The parenteral formulations of TMC278 can be administered at time intervals mentioned above. In one embodiment the time interval is in the range of one to two weeks, or two to three weeks, or three to four weeks. In another embodiment the time interval is in the range of one to two months, or two to three months, or three to four months. The time interval may be at least one week, but may also be several weeks, e.g. 2, 3, 4, 5 or 6 weeks, or at time intervals of one month, or of several months, e.g. 2, 3, 4, 5 or 6 months or even longer, e.g. 7, 8, 9 or 12 months. In one embodiment, the parenteral formulation is administered at a time interval of one, two or three months. These longer periods between each administration of the parenteral formulation consist in an even further improvement of "pill burden" and compliance. To further improve compliance, patients can be instructed to take their medication at a certain day of the week, where the formulation is administered on a weekly schedule, or at a certain day of the month in case of a monthly schedule. The time intervals between each administration of a parenteral formulation of TMC278 may vary. For example, the intervals may be shorter where the blood plasma levels of TMC278 are deemed too low, e.g. when these approach the minimum blood plasma level specified hereinafter. The intervals may be longer where the blood plasma levels of TMC278 are deemed too high. In one embodiment, the parenteral formulations of TMC278 are administered at the same time intervals, for example every week, or every two weeks, every month, or at every time interval mentioned herein. Having time intervals of the same length has the advantage that the administration is e.g. at the same day in the week, or the same day in the month, thereby contributing to compliance of the therapy.

As used herein the term "treatment of HIV infection" relates to a situation of the treatment of a subject being infected with HIV. The term "subject" in particular relates to a human being.

Preferably the parenteral formulation is administered in a single administration, for example by one injection after a time interval of at least one week, e.g. by one injection every week or by one injection every month.

The dose of TMC278 administered, which is the amount of TMC278 in the parenteral formulation for use in the invention, is selected such that the blood plasma concentration of TMC278 is kept during a prolonged period of time above a minimum blood plasma level. The term "minimum blood plasma level" in this context refers to the lowest efficacious blood plasma level, the latter being that blood plasma level of TMC278 that provides effective treatment of HIV, or in alternative wording, that blood plasma level of TMC278 that is effective in suppressing HIV.

The terms "effective treatment of HIV", "effectively suppress viral load", or similar terms mean that the treatment results in the multiplication of HIV being suppressed to such a level that the viral load is relatively low, for example to a viral load (represented as the number of copies of viral RNA in a specified volume of serum) below about 200 copies/ml, in particular below about 100 copies/ml, more in particular below 50 copies/ml, specifically below the detection limit of the virus. An "effective amount" refers to such an amount of TMC278 that, upon administration, reduces the viral load, in particular reduces the viral load below the number of copies mentioned above. The term "effective blood plasma levels" refers to those blood plasma levels of TMC278 that result in a reduction of the viral load, in particular below the number of copies mentioned above.

In particular, the blood plasma level of TMC278 is kept at a level above a minimum blood plasma level that is in the range of about 5 to about 500 ng/ml, or about 5 ng/ml to about 200 ng/ml, or about 5 ng/ml to about 100 ng/ml, or about 10 ng/ml to about 50 ng/ml. More in particular, the blood plasma level of TMC278 is kept at a level above a minimum blood plasma level that is in the range of about 5 to about 50 ng/ml, or in the range of about 10 to about 50 ng/ml, or in the range of about 15 to about 50 ng/ml. In certain embodiments, the blood plasma level of TMC278 is kept at a level above a minimum blood plasma level of about 10 ng/ml, or about 15 ng/ml, or about 20 ng/ml, or about 40 ng/ml, or about 100 ng/ml, or about 200 ng/ml, or about 400 ng/ml. In a particular embodiment, the blood plasma level of TMC278 is kept above a level of about 13.5 ng/ml, or about 20.3 ng/ml.

The plasma levels of TMC278 should be kept above these threshold blood plasma levels because at lower levels the drug may no longer be effective thereby increasing the risk of mutations.

The dose of TMC278 administered also depends on the time interval at which it is administered. The dose will be higher where administrations are less frequent.

The dose to be administered each time should be calculated on a basis of about 0.5 mg/day to about 50 mg/day, or about 1 mg/day to about 20 mg/day, or about 1 mg/day to about 10 mg/day, or about 3 mg/day to about 7 mg/day, e.g. about 5 mg/day. This corresponds to a weekly dose of about 3.5 mg to about 350 mg, or about 7 mg to about 140 mg, or about 7 mg to about 70 mg, or about 21 mg to about 49 mg e.g. about 35 mg or a monthly dose of from about 15 mg to about 1,500 mg, or about 30 mg to about 600 mg, or about 30 mg to about 300 mg, or about 90 mg to about 210 mg, e.g. about 150 mg. Multiplying the above mentioned per day doses by the number of days in a given time interval gives the doses or dose ranges for that time interval.

It has been found that, once administered, the blood plasma levels of TMC278 are more or less stable, i.e. they fluctuate within limited margins. The blood plasma levels have been found to approach a steady state mode during a prolonged period of time. By "steady state" is meant the condition where the amount of drug present in the blood plasma of a subject stays at more or less the same level over a prolonged period of time. The plasma levels of TMC278 generally do not show any drops below the minimum plasma level at which the drug is effective. The term "stays at more or less the same level" does not exclude that there can be small fluctuations of the plasma concentrations within an acceptable range, e.g. within about 30% in particular, within about 20%, further in particular within about 10%.

The concentration (or "C") of TMC278 in the plasma of a subject is generally expressed as mass per unit volume, typically nanograms per milliliter (ng/ml). For convenience, this concentration may be referred to as "plasma drug concentration" or "plasma concentration" herein.

The plasma concentrations of TMC278 may reach relatively high levels, without causing significant side effects but should not exceed a maximum plasma level (or $C_{max}$), which is the blood plasma level where TMC278 causes significant side effects. As used herein, the term 'significant side effects' means that the side effects are present in a relevant patient population to an extend that the side effects affect the patients' normal functioning. The $C_{max}$ for TMC278 can be determined from the extrapolation of test data in cellular assays or from the evaluation of clinical testing and preferably should not exceed a value of about 1000 ng/ml.

In some instances there may be a small initial plasma concentration peak shortly after administration, after which the plasma levels achieve a 'steady-state' as mentioned above.

The parenteral TMC278 formulations may be administered by intravenous injection or preferably by subcutaneous or intramuscular administration.

The present invention is based on the use of parenteral formulations of the active ingredient TMC278 and therefore the nature of the carrier will have to be selected such as to suit parenteral administration. The carrier will be liquid and may be oily but in most cases will be aqueous. In the latter instance, the carrier comprises sterile water, though other ingredients may be included. The carrier may also contain a co-solvent, for example an alcohol such as ethanol, propanol, ethylene glycol, propylene glycol, or a polymer acting as co-solvent such as polyethylene glycol (PEG) or polyethoxylated castor oil (Cremophor®).

To enhance solubility of the active compound additional ingredients may be added to the parenteral formulations of the active ingredient TMC278 that have a solubility promoting effect such as solubilizers and surfactants, or ingredients being both a surfactant and solubilizer. Examples of such additional ingredients are cyclodextrins or cyclodextrin derivatives. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD).

Other such ingredients with surfactant properties are poloxamers, which are polyoxyethylene, polyoxypropylene block copolymers that conform generally to the formula $HO—[CH_2CH_2O]_x—[CH(CH_3)CH_2O]_y—[CH_2CH_2O]_z—H$ wherein x, y and z can have various values, available under the tradename Pluronic®, e.g. Pluronic® F108, corresponding to poloxamer 338 in which the average values of x, y and z are respectively 128, 54 and 128. Still other such ingredients are the α-tocopheryl polyethylene glycol succinates, in particular Vitamin E TGPS; the polyoxyethylene sorbitan fatty acid esters (also referred to as polysorbates), available under the tradename Tween®, e.g. Tween® 80; the polyethylene glycols (PEGs) such as PEG 400.

The parenteral formulations of the active ingredient TMC278 may further comprise suspending agents and buffers and/or pH adjusting agents, and optionally preservatives and isotonizing agents. Particular ingredients may function as two or more of these agents simultaneously, e.g. behave like a preservative and a buffer, or behave like a buffer and an isotonizing agent.

Buffering and pH adjusting agents should be used in an amount sufficient to render the dispersion neutral to very slightly basic (up to pH 8.5), preferably in the pH range of 7 to 7.5. Particular buffers are the salts of week acids. Buffering and pH adjusting agents that can be added may be selected from tartaric acid, maleic acid, glycine, sodium lactate/lactic acid, ascorbic acid, sodium citrates/citric acid, sodium acetate/acetic acid, sodium bicarbonate/carbonic acid, sodium succinate/succinic acid, sodium benzoate/benzoic acid, sodium phosphates, tris(hydroxymethyl)aminomethane, sodium bicarbonate/sodium carbonate, ammonium hydroxide, benzene sulfonic acid, benzoate sodium/acid, diethanolamine, glucono delta lactone, hydrochloric acid, hydrogen bromide, lysine, methanesulfonic acid, monoethanolamine, sodium hydroxide, tromethamine, gluconic, glyceric, gluratic, glutamic, ethylene diamine tetraacetic (EDTA), triethanolamine, including mixtures thereof.

Preservatives comprise antimicrobials and anti-oxidants which can be selected from the group consisting of benzoic acid, benzyl alcohol, butylated hydroxyanisole (BHA), butylated hydroxytoluene (BHT), chlorbutol, a gallate, a hydroxybenzoate, EDTA, phenol, chlorocresol, metacresol, benzethonium chloride, myristyl-γ-piccolinium chloride, phenylmercuric acetate and thimerosal. Radical scavengers include BHA, BHT, Vitamin E and ascorbyl palmitate, and mixtures thereof. Oxygen scavengers include sodium ascorbate, sodium sulfite, L-cysteine, acetylcysteine, methionine, thioglycerol, acetone sodium bisulfate, isoacorbic acid, hydroxypropyl cyclodextrin. Chelating agents include sodium citrate, sodium EDTA and malic acid.

Isotonizing agents_are, for example, sodium chloride, dextrose, sucrose, fructose, trehalose, mannitol, glycerin, sorbitol, xylitol, lactose, sodium sulfate. The suspensions conveniently comprise from 0 to 10% (w/v), in particular 0 to 6% of isotonizing agent. Typical nonionic isotonifiers are preferred, in particular glycerin, as electrolytes may affect colloidal stability.

In some instances, the parenteral formulations with TMC278 may be formulated with or in a suitable controlled release or sustained release or sustained release carrier.

For example, the active ingredient TMC278 may be encapsulated into small polymeric microspheres that degrade slowly and release the active ingredient at a controlled rate. One form of microspheres are those wherein the active ingredient is encapsulated in a biodegradable polymer such as polylactide/polyglycolide polymers or copolymers. Another polymer based technology is the ReGel™ technology from MacroMed, which uses triblock copolymers of poly(lactide-co-glycolide) and polyethylene glycol. These are thermosensitive and biodegradable polymers that become a gel upon heating and return to their original state upon cooling. These polymers/hydrogels systems are applied as solutions at administration temperature and become insoluble gels at the injection site. An insoluble gel depot is formed immediately upon injection and remains at the site for a period of several weeks. Drug release is controlled through a combination of diffusion from and degradation of the polymer. Another type of sustained release injectable dosage forms are based on liposomal systems, which can be used in case of lipophilic drugs or lypophilically modified pro-drugs. The liposome particles can be coated, e.g. with polyethylene glycol to evade the immune system. Still another type of sustained release injectable dosage forms are the microscopic, spherical particles known as DepoFoam™ from SkyePharma. These particles, essentially lipid in nature, contain a multitude of small aqueous chambers encapsulating the drug to be delivered.

Preferably the carrier is selected such that the dosage form is well-tolerated, with minimal or no side effects.

The parenteral dosage forms of TMC278 when administered in accordance with the present invention provide effective treatment of HIV infection in that the viral load is reduced while keeping viral replication suppressed. The limited number of drug administrations and the lack of undesirable side effects after each administration adds to the patients' compliance with the therapy. Patients' compliance may further be improved when selecting parenteral formulations showing good local tolerance and ease of administration.

EXAMPLE

This example shows a study aimed at demonstrating that the administration of a parenteral formulation of TMC278 results in stable blood plasma levels during a prolonged period of time. By increasing the dose of TMC278 of the parenteral formulation higher blood plasma levels are obtained, for example a dose of about 10 mg/kg is expected to result in effective blood plasma levels. By administering the parenteral formulation intermittently at time intervals of one month, stable blood plasma levels of TMC278 are obtained, effectively suppressing viral multiplication.

The study was performed in order to study the plasma kinetics and the absolute bioavailability of TMC278 in the beagle dog after single intramuscular administration (IM) of an aqueous 30% dimethylacetamide (DMA)/50% polyethylene glycol 400 (PEG400) solution of TMC278 at 2.5 mg/kg. The dogs were dosed IM.

Two male beagle dogs (dog No. 16924 and 16854), approximately 3 years old and weighing between 11 and 12 kg at the start of the experimental phase, were used in the present experiment. The dogs were dosed intramuscularly at 0.1 ml/kg body weight by injecting the formulation in the left (dog No. 16924) or right (dog No. 16854) m. biceps femoris.

One day before dose administration, TMC278 was formulated in an aqueous 30% (w/v) DMA/50% (w/v) PEG400 solution at 25 mg/ml. The ingredients of the solution were: TMC278, DMA 30% (w/v), PEG 400 50% (w/v) and pyrogenic free water. The content of TMC278 in the formulation was checked using LC. The concentration of TMC278 in the formulation was 25 mg/ml.

Blood samples (4 ml on EDTA) were taken from a jugular vein from the dogs at 0 (=predose), 0.5, 1, 2, 4, 8, 24, 32, 48, 72, 96, 144, 192, 240 and 312 h after dose administration. After sampling, the blood samples were immediately placed on melting ice and protected from light. Blood samples were centrifuged at approximately 1900×g for 10 minutes at 5° C. to allow plasma separation. Immediately after separation, plasma samples were protected from light, placed on melting ice and stored at ≤−18° C. until analysis. Frozen plasma samples were transferred for bioanalysis. Since TMC278 was still detectable in the plasma samples at 312 h post-dose, additional blood samples of both dogs were collected on the days 36, 50, 64, 78, 92, 106, 120, 134 and 148. These samples were analogously processed and analysed.

On day 232 post-dose, a biopsy was performed (dog No. 16924 only) on the iliac lymph node (at the side of injection), on a muscle from the non-injected hind leg and on a muscle at the side of injection after ultrasonographic examination. All tissue samples were protected from light as much as possible and stored on melting ice. All samples were protected from light and stored at ≤−18° C. Finally, an additional blood sample was collected on day 272. This sample was processed and analysed similarly to the other blood samples.

The concentration of TMC278 in dog plasma was determined by a qualified research LC-MS/MS method after solid phase extraction (SPE). Plasma concentrations of TMC278 were determined after proper sample clean up. The samples (0.1 ml aliquots of plasma) were extracted using a solid phase extraction method (Bond Elut Certify solid phase columns, 130 mg, SPE, Varian). The SPE column was conditioned with 3 ml methanol, 3 ml water and 1 ml acetic acid 1 M.

After addition of 3 ml acetic acid to 0.1 ml aliquots of plasma, the samples were extracted on the column followed by washing the column with 1 ml water, 1 ml acetic acid 1 M and 3 ml methanol. The column was eluted with 3 ml methanol/$NH_4OH$ 25% (98:2, v/v). The extract was evaporated to dryness and reconstituted in 150 μl of ammonium formate 0.01 M (adjusted to pH 4 with formic acid)/methanol (50/50). 20 μl-aliquots were injected onto a reversed phase LC-column (100×4.6 mm ID, packed with 3 μm Hypersil C18 BDS) with a flow of 800 μl/min. The elution mixture was ammonium formate 0.01 M (adjusted to pH 4 with formic acid)/methanol (40:60, v/v). The flow-rate to the mass spectrometer was about 100 μl/min after splitting. LC-MS/MS analysis was carried out on an API-3000 system (Applied Biosystems), coupled to an HPLC-system.

The concentration of TMC278 in dog tissue samples was also determined by a qualified research LC-MS/MS method. Tissues samples were homogenized with a 10-fold dilution in Milli-Q water by means of an Ultra-Turrax. The tissue homogenates (200 μl aliquot) were extracted by adding of 600 μl methanol (containing TMC278 and/or R152929 and/or methanol). After vortexing and centrifugation, the supernatant was transferred to an HPLC vial and 20 μl aliquots were injected. The LC and the MSMS conditions were the same as described above. The lower limit of quantification was 10.0 ng/g tissue. Samples were protected from light during the bioanalytical analysis.

Individual plasma concentration-time profiles were subjected to a non-compartmental pharmacokinetic analysis. Peak plasma concentrations ($C_{max}$) and corresponding peak times ($T_{max}$) were determined. The AUC from time 0 to time t ($AUC_{0-t}$, where t is the time point associated with the last measurable concentration above the limit of quantification) was calculated by means of the linear/log trapezoidal rule: i.e. linear trapezoidal rule up to $T_{max}$: $AUC_{0-Tmax}=\Sigma[(t_{i+1}-t_i)\cdot(C_i+C_{i+1})/2]$, and log trapezoidal for the remainder of the curve: $AUC_{Tmax-t}=\Sigma[(t_{i+1}-t_i)\cdot(C_i-C_{i+1})/\ln(C_i/C_{i+1})]$, $C_i$ and $C_{i+1}$ being the plasma concentrations at times $t_i$ and $t_{i+1}$, respectively. The area under the curve extrapolated to infinity ($AUC_{0-\infty}$) and the absolute bioavailability of TMC278 in the present formulation could not be calculated adequately since plasma concentrations remained fairly constant or slightly increased between 72 h and 312 h after dosing. The half-life was calculated between 1 h and 24 h ($t_{1/2,\ 1\text{-}24\ h}$) or 8 h and 24 h ($t_{1/2,\ 8\text{-}24\ h}$) and between 24 h and 72 h post-dose ($t_{1/2,\ 24\text{-}72\ h}$) according to $t_{1/2}=\ln(2)/k$, with k corresponding to the rate constant over the respective time ranges. Mean (n=2) plasma concentrations and pharmacokinetic parameters were calculated.

Individual and mean (n=2) plasma concentrations and/or some basic pharmacokinetic parameters are reported in Table 1 and Table 2. Tissue levels (iliac lymph node, muscle), collected on day 232 after dosing, are showed in the Table 3.

After intramuscular administration of an aqueous 30% DMA/50% PEG400 solution of TMC278 at 2.5 mg/kg, mean peak plasma concentrations ($C_{max}$) amounted to 31.9 ng/ml. The individual peak plasma levels were reached within 1 to 8 h after dosing. After $C_{max}$, plasma levels declined rapidly till 24 h post-dose, followed by a more slowly decline up to 72 h after dosing with an half-life ($t_{1/2,\ 24\text{-}72\ h}$) of 63 h. After 72 h post-dose, plasma levels remained fairly constant or slightly increased up to 312 h post-dose. The mean $AUC_{0\text{-}312\ h}$ value amounted to 1863 ng·h/ml.

Since plasma concentrations remained fairly constant or slightly increased between 72 h and 312 h post-dose, additional blood samples were taken on the days 36, 50, 64, 78, 92, 106, 120, 134 and 148. During this wash-out period, plasma levels remained fairly constant (range: 1.24-4.23 ng/ml). Therefore, a biopsy was performed on the iliac lymph node (at the side of injection), on a muscle from the non-injected hind leg and on a muscle at the side of injection. The biopsy was performed on day 232 in dog No. 16924 only. The levels of TMC278 in the muscles were below the limit of quantification (10.0 ng/g). The level in the lymph node amounted to 72.6 ng/g, which was high with respect to the plasma concentrations on day 148 (i.e. on average 1.33 ng/ml) and on day 272 (<1.00 ng/ml).

TABLE 1

Individual and mean (n = 2) plasma concentrations (ng/ml) and some basic pharmacokinetic parameters of TMC278 in beagle dogs after single intramuscular administration of an aqueous 30% DMA/50% PEG400 solution of TMC278 at 2.5 mg/kg.

| | | Dosage group 2.5 mg/kg Dog No. | | |
|---|---|---|---|---|
| Time (h) | | 16854 | 16924 | Mean |
| 0 | | <1.00 | <1.00 | <1.00 |
| 0.5 | | 13.5 | 21.3 | 17.4 |
| 1 | | 17.0 | 23.8 | 20.4 |
| 2 | | 20.6 | 20.9 | 20.8 |
| 4 | | 27.2 | 17.1 | 22.2 |
| 8 | | 39.9 | 15.1 | 27.5 |
| 24 | | 11.4 | 7.70 | 9.55 |
| 32 | | 10.7 | 6.65 | 8.68 |
| 48 | | 9.03 | 6.03 | 7.53 |
| 72 | | 7.37 | 3.90 | 5.64 |
| 96 | | 6.40 | 3.97 | 5.19 |
| 144 | | 3.19 | 3.65 | 3.42 |
| 192 | | 2.80 | 3.57 | 3.19 |
| 240 | | 6.16 | 4.38 | 5.27 |
| 312 | | 4.24 | 5.97 | 5.11 |
| $C_{max}$ | ng/ml | 39.9 | 23.8 | 31.9 |
| $T_{max}$ | h | 8 | 1 | 5 |
| $t_{1/2,1\text{-}24h}$ | h | 8.9[1)] | 15.1 | NC[2)] |
| $t_{1/2,24\text{-}72h}$ | h | 75.2 | 51.0 | 63.1 |
| $AUC_{0\text{-}312h}$ | ng · h/ml | 2122 | 1603 | 1863 |

[1)] $t_{1/2,8\text{-}24h}$

[2)] NC: Not calculated.

TABLE 2

Individual and mean (n = 2) plasma concentrations (ng/ml) of TMC278 in beagle dogs during the wash-out period after single intramuscular administration of an aqueous 30% DMA/50% PEG400 solution of TMC278 at 2.5 mg/kg.

| | Dosage group 2.5 mg/kg Dog No. | | |
|---|---|---|---|
| Day | 16854 | 16924 | Mean |
| 36 | 3.66 | 3.05 | 3.36 |
| 50 | 4.10 | 2.12 | 3.11 |
| 64 | 2.18 | 2.42 | 2.30 |
| 78 | 2.62 | 1.69 | 2.16 |
| 92 | 2.32 | 2.51 | 2.42 |
| 106 | 2.02 | 1.75 | 1.89 |
| 120 | 1.87 | 4.23 | 3.05 |
| 134 | 1.67 | 1.61 | 1.64 |
| 148 | 1.41 | 1.24 | 1.33 |
| 272 | ND[1)] | <1.00 | ND |

[1)] ND: Not determined.

TABLE 3

Tissue concentrations (ng/g) of TMC278 in beagle dogs on day 232 after single intramuscular administration of an aqueous 30% DMA/50% PEG400 solution of TMC278 at 2.5 mg/kg.

| Tissue | Dosage group 2.5 mg/kg Dog No. 16924 |
|---|---|
| iliac lymph node at the side of injection | 72.6 |
| muscle from the non-injected hind leg | <10.0 |
| muscle at the side of injection | <10.0 |

The invention claimed is:

1. A method of treating HIV *infection* in a subject comprising administering to the subject [a solution] *an aqueous parenteral formulation* comprising an amount of 4-[[4-[[4-(2-cyanoethenyl)-2,6-dimethylphenyl]amino]-2-pyrimidinyl]amino]benzonitrile (TMC278) or a pharmaceutically acceptable acid-addition salt thereof, and a carrier, wherein the [solution] *aqueous parenteral formulation* is administered intermittently by subcutaneous or intramuscular administration at a time interval that is once every [one] month or once every four weeks, and wherein the amount of TMC278, or the pharmaceutically acceptable acid-addition salt thereof, is effective in keeping a minimum blood plasma level of TMC278 in the subject during the time interval*, and the minimum blood plasma level is about 5 ng/mL to about 500 ng/mL.*

2. The method according to claim 1, wherein the [solution] *aqueous parenteral formulation* is administered intramuscularly.

[3. The method according to claim 1, wherein the minimum blood plasma level is about 5 ng/mL to about 500 ng/mL.]

4. The method according to claim 1, wherein the minimum blood plasma level is about 5 ng/mL to about 200 ng/mL.

5. The method according to claim 1, wherein the minimum blood plasma level is about 5 ng/mL to about 100 ng/mL.

6. The method according to claim 1, wherein the minimum blood plasma level is about 10 ng/mL to about 50 ng/mL.

7. The method according to claim 1, wherein the subject's HIV viral load is below about 200 copies/mL, prior to administration of the [solution] *aqueous parenteral formulation.*

8. The method according to claim 1, wherein the [solution is an aqueous solution] *amount of TMC278, or the pharmaceutically acceptable acid addition salt thereof, constitutes a dose calculated on a basis of about 0.5 mg/day to about 50 mg/day of the time interval.*

9. The method according to claim 1, wherein the time interval is once every four weeks.

10. The method according to claim 1, wherein the time interval is once every one month.

11. The method according to claim 1, wherein the TMC278 *or the pharmaceutically acceptable acid-addition salt thereof* is E-TMC278.

12. The method according to claim 1, wherein the carrier comprises polyethyleneglycol.

13. The method according to claim 8, wherein the carrier comprises polyethyleneglycol.

*14. The method according to claim 1, wherein the subject's HIV viral load is below 50 copies/ml, prior to administration of the aqueous parenteral formulation.*

*15. The method according to claim 2, wherein the TMC278 or the pharmaceutically acceptable acid-addition salt thereof is TMC278.*

*16. The method according to claim 2, wherein the TMC278 or the pharmaceutically acceptable acid-addition salt thereof is E-TMC278.*

*17. The method according to claim 8, wherein the aqueous parenteral formulation is administered intramuscularly.*

*18. The method according to claim 17, wherein the TMC278 or a pharmaceutically acceptable acid-addition salt thereof is E-TMC278.*

*19. The method according to claim 18, wherein the amount of E-TMC278 is a dose calculated on a basis of about 20 mg/day of the time interval.*

*20. The method according to claim 18, wherein the amount of E-TMC278 is about 600 mg.*

*21. The method according to claim 16, wherein the time interval is once every month.*

*22. The method according to claim 18, wherein the time interval is once every month.*

*23. The method according to claim 19, wherein the time interval is once every month.*

*24. The method according to claim 20, wherein the time interval is once every month.*

*25. The method according to claim 21, wherein the intramuscular administration is administered via a single administration.*

*26. The method according to claim 22, wherein the intramuscular administration is administered via a single administration.*

*27. The method according to claim 23, wherein the intramuscular administration is administered via a single administration.*

*28. The method according to claim 24, wherein the intramuscular administration is administered via a single administration.*

*29. The method according to claim 25, wherein blood plasma levels of E-TMC278 approach a steady state mode during a prolonged period of time.*

*30. The method according to claim 26, wherein blood plasma levels of E-TMC278 approach a steady state mode during a prolonged period of time.*

*31. The method according to claim 27, wherein blood plasma levels of E-TMC278 approach a steady state mode during a prolonged period of time.*

*32. The method according to claim 28, wherein blood plasma levels of E-TMC278 approach a steady state mode during a prolonged period of time.*

*33. The method according to claim 27, wherein the E-TMC278 is suspended in the aqueous parenteral formulation.*

*34. The method according to claim 28, wherein the E-TMC278 is suspended in the aqueous parenteral formulation.*

*35. The method according to claim 18, wherein the minimum blood plasma level is above 13.5 ng/mL.*

*36. The method according to claim 23, wherein the minimum blood plasma level is above 13.5 ng/mL.*

*37. The method according to claim 24, wherein the minimum blood plasma level is above 13.5 ng/mL.*

*38. The method according to claim 27, wherein the minimum blood plasma level is above 13.5 ng/mL.*

*39. The method according to claim 28, wherein the minimum blood plasma level is above 13.5 ng/mL.*

*40. The method according to claim 18, wherein the aqueous parenteral formulation further comprises poloxamer 338.*

*41. The method according to claim 40, wherein the minimum blood plasma level is above 13.5 ng/mL.*

*42. The method according to claim 41, wherein the intramuscular administration is administered via a single administration.*

*43. The method according to claim 18, wherein the time interval is once every four weeks.*

*44. The method according to claim 43, wherein the minimum blood plasma level is above 13.5 ng/mL.*

*45. The method according to claim 44, wherein the intramuscular administration is administered via a single administration.*

*46. A method of treating HIV infection in a subject comprising administering to the subject an aqueous parenteral formulation comprising*

*an amount of 4-[[4-[[4-(2-cyanoethenyl)-2,6-dimethylphenyl]amino]-2-pyrimidinyl]amino]benzonitrile (TMC278) and a carrier,*

*wherein the aqueous parenteral formulation is administered intermittently by intramuscular administration at a time interval that is once every two months,*

*and wherein the amount of TMC278 is effective in keeping a minimum blood plasma level of TMC278 in the subject during the time interval, and the minimum blood plasma level is about 5 ng/mL to about 500 ng/mL.*

*47. The method according to claim 46, wherein the minimum blood plasma level is about 5 ng/mL to about 200 ng/mL.*

*48. The method according to claim 46, wherein the minimum blood plasma level is about 5 ng/mL to about 100 ng/mL.*

*49. The method according to claim 46, wherein the minimum blood plasma level is about 10 ng/mL to about 50 ng/mL.*

*50. The method according to claim 46, wherein the subject's HIV viral load is below about 200 copies/mL, prior to administration of the aqueous parenteral formulation.*

*51. The method according to claim 46, wherein the subject's HIV viral load is below about 50 copies/mL, prior to administration of the aqueous parenteral formulation.*

*52. The method according to claim 46, wherein the amount of TMC278 is a dose calculated on a basis of about 0.5 mg/day to about 50 mg/day of the time interval.*

*53. The method according to claim 46, wherein the amount of the TMC278 is a dose calculated on a basis of about 10 mg/day to about 20 mg/day of the time interval.*

*54. The method according to claim 46, wherein the TMC278 is E-TMC278.*

*55. The method according to claim 54, wherein the amount of E-TMC278 is a dose calculated on a basis of about 0.5 mg/day to about 50 mg/day of the time interval.*

*56. The method according to claim 55, wherein the minimum blood plasma level is above 13.5 ng/mL.*

*57. The method according to claim 54, wherein the amount of the E-TMC278 is a dose calculated on a basis of about 10 mg/day to about 20 mg/day of the time interval.*

*58. The method according to claim 54, wherein the intramuscular administration is via a single administration.*

*59. The method according to claim 58, wherein blood plasma levels of E-TMC278 approach a steady state mode during a prolonged period of time.*

*60. The method according to claim 55, wherein the aqueous parenteral formulation further comprises poloxamer 338.*

*61. The method according to claim 60, wherein the minimum blood plasma level is above 13.5 ng/mL.*

*62. The method according to claim 61, wherein the intramuscular administration is administered via a single administration.*

*63. The method according to claim 55, wherein the intramuscular administration is administered via a single administration.*

*64. The method according to claim 63, wherein blood plasma levels of E-TMC278 approach a steady state mode during a prolonged period of time.*

*65. The method according to claim 63, wherein the E-TMC278 is suspended in the aqueous parenteral formulation.*

* * * * *